United States Patent [19]

Schmidt

[11] Patent Number: 5,286,871
[45] Date of Patent: Feb. 15, 1994

[54] STABILIZED AQUEOUS SOLUTIONS OF 3-ISOTHIAZOLONES

[75] Inventor: Hans-Jügen Schmidt, Speyer, Fed. Rep. of Germany

[73] Assignee: Thor Chemi GmbH, Fed. Rep. of Germany

[21] Appl. No.: 868,312

[22] Filed: Apr. 14, 1992

Related U.S. Application Data

[63] Continuation of Ser. No. 582,499, Sep. 14, 1990, Pat. No. 5,153,213.

[30] Foreign Application Priority Data

Nov. 10, 1989 [EP] European Pat. Off. ........ 89-120912.4

[51] Int. Cl.$^5$ .............................................. A01N 43/80
[52] U.S. Cl. .................................................... 548/213
[58] Field of Search ......................................... 548/213

[56] References Cited

U.S. PATENT DOCUMENTS

| | | | |
|---|---|---|---|
| 4,150,026 | 4/1979 | Miller et al. | 548/213 |
| 4,920,137 | 4/1990 | Segall et al. | 548/213 |
| 4,975,109 | 12/1990 | Friedman, Jr. et al. | 548/213 |

FOREIGN PATENT DOCUMENTS 351772 1/1990 European Pat. Off. .

OTHER PUBLICATIONS

Research Disclosure, 160, 28 (1977).
Aldrich, p. 690 (1992).

*Primary Examiner*—Robert Gerstl
*Attorney, Agent, or Firm*—Hedman, Gibson & Costigan

[57] ABSTRACT

Stabilized aqueous solutions of one or more 3-isothiazolones of the general Formula I or II

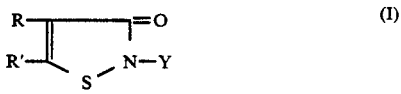

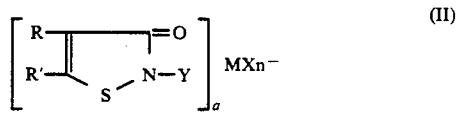

are given, characterized in that they contain at least 0.1 wt. % taken on the total solution of a 3-isothiazolone, of a hydroperoxide-free organic and/or manganese-free inorganic oxidizing agent, as well as optionally a stabilizer for the oxidizing agent.

12 Claims, No Drawings

STABILIZED AQUEOUS SOLUTIONS OF 3-ISOTHIAZOLONES

This is a continuation of application Ser. No. 07/582,499 filed Sep. 14, 1990 now U.S. Pat. No. 5,153,213.

The invention relates to stabilized aqueous solutions of one or more 3-isothiazolones with oxidizing agents, alone, or with co-stabilizers in accordance with the claims herein, as well as the use of such stabilized solutions.

BACKGROUND OF THE INVENTION

3-Isothiazolones are known compounds. In their practical use, for example, as bactericidal, fungicidal or algicidal materials, they have the disadvantage that they decompose relatively easily in solution and thereby become ineffective and in some cases also form undesired by-products.

In the past, attempts have been made to improve the stability of 3-isothiazolones by the addition of, for example, solvents, chlorides, nitrates or other salts, formaldehyde, formaldehyde-forming materials as well as ortho-esters or other organic compounds. Such methods are described, for example, in U.S. Pat. Nos. 3,870,795 and 4,067,878 (metal nitrates and nitrites); U.S. Pat. Nos. 4,129,448 and 4,165,318 (formaldehyde); and U.S. Pat. No. 4,824,957 (organic hydroxylic solvents). EP-A 147,223 discloses preservative or disinfectant compositions comprising an organic biocide (including isothiazolones) and an organic hydroperoxide (aliphatic or aromatic). This patent does not disclose stabilizing properties of hydroperoxides. In EP-A 0 315 464 stabilized 3-isothiazolone-containing mixtures are described. Orthoesters of formic, acetic, or benzoic acid serve as stabilizers therein. However, this is very costly.

EP-A 0 300 483 discloses 3-isothiazolones which can be stabilized by the addition of relatively complex synthetic organic compounds such as hydroquinones or quinones, alone, or in combination with synergists such as metal nitrates and potassium permanganate.

In many cases of the use of 3-isothiazolones, it is desirable for various reasons to diminish the content of the above-noted known stabilizers in the biocides containing the 3-isothiazolones. For example, it is also known that dispersions or emulsions which require microbiocidal protection are sensitive with respect to the addition of salts. This is true particularly if the salts contain divalent ions. Promoted by poor mixing, coagulates then easily arise, which adversely affect the quality of the dispersion or emulsion.

Furthermore, the microbiocidally active components can become enclosed in these coagulates. Thereby only fractions or in an unfavorable case no microbiocidally-active materials are available. This is especially true if the products to be preserved are filtered.

These undesired actions of the above-noted components in biocides containing isothiazolones also arise in some formulations which have been stabilized with low salt concentrations or salt free hydroxyl group-containing solvents.

Furthermore, there are formulations which should contain none or only a small concentration of chloride since otherwise damaging incompatibilities arise. Additionally, by a diminution of the chloride content, the corrosion action of the formulation is also reduced.

In isothiazolone formulations which are stabilized by nitrates, there is the danger of the introduction or the formation of nitrosamines. The latter are suspected of having carcinogenic properties. Accordingly there is a substantial need to avoid nitrates for stabilization or to reduce their quantity. In the case of formaldehyde and formaldehyde-yielding materials as stabilizers, it has been shown at least in animal experiments that formaldehyde acts carcinogenically.

The object underlying the present invention is to provide a method for the stabilization of aqueous solutions of one or more isothiazolones which makes it possible to reduce or even wholly avoid the content previously necessary for stabilization of chloride, nitrate (and the undesired nitrosamine formation bound up with that), nitrite, other metal salts, formaldehyde, formaldehyde-yielding materials and/or solvents (with the exception of water).

SUMMARY OF THE INVENTION

In accordance with the present invention there are provided stabilized compositions comprising:

(A) an aqueous solution comprising at least one 3-isothiazolone compound of the general Formula I or II:

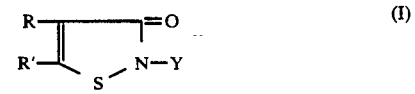

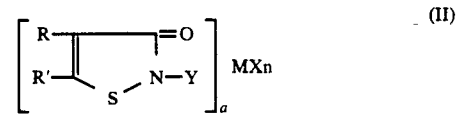

wherein

Y is a hydrogen atom or an unsubstituted alkyl group of from about 1 to about 18 carbon atoms, an unsubstituted or halo substituted alkenyl or alkynyl group of from about 2 to about 8 carbon atoms, an unsubstituted or substituted cycloalkyl group of from about 5 to about 8 carbon atoms, an unsubstituted or substituted aralkyl group of from about 7 to about 11 carbon atoms or an unsubstituted or substituted aryl group of from about 6 to about 10 carbon atoms;

R and R' are each selected from hydrogen, halogen or an alkyl group of from about 4 to about 8 carbon atoms;

M is a cation selected from a metal cation, an ammonium cation or an ammonium cation substituted with at least one organic group, a pyridinium cation or a pyrimidinium cation;

X is an anion forming a compound with the cation M; and a is 1 or 2 and n is a whole number which satisfies the valence of the cation M when completely reacted with anion X, alone, or in further combination with a stabilizer for I or II; and (B) a small effective amount of:

(i) a hydroperoxide-free organic oxidizing agent, alone, or in further combination with a stabilizer therefor;

(ii) a manganese-free inorganic oxidizing agent, alone, or in further combination with a stabilizer therefor; or (iii) a mixture of (i) and (ii).

Among the preferred features of the invention are compositions as defined above wherein component (A) comprises from about 0.5 to about 3 wt. % of said 3-isothiazolone and component (B) comprises at least about 0.1 wt. % based on the total weight of (A) and (B); compositions as defined above wherein said inorganic oxidizing agent (i) comprises hydrogen peroxide, sodium perborate or a mixture thereof; compositions as defined above wherein said organic oxidizing agent (ii) comprises benzoyl peroxide, tert.-butyl peroxide or a mixture thereof; compositions as defined above which also include diethylene triamine pentacetic acid as a stabilizer for the oxidizing agent; compositions as defined above wherein said oxidizing agent (B) is present in an amount of from about 0.1 to about 3 wt. % based on the total weight of (A) and (B); and compositions as defined above which also include a stabilizer for the oxidizing agent and said stabilizer is present in an amount of from about 1 to about 20 parts per million by weight, based on the total weight of (A) and (B).

Special mention is made of compositions as defined above wherein said 3-isothiazolone comprises: 5-chloro-2-methyl-3-isothiazolone; 2-methyl-3-isothiazolone; 2-octyl-3-isothiazolone; 4,5-dichloro-2-cyclohexyl-3-isothiazolone; 4,5-dichloro-2-octyl-3-isothiazolone; or a mixture of any of the foregoing.

Particularly preferred are compositions as defined above comprising from about 1.0 to about 1.5 wt. % of a 5-chloro-3-isothiazolone, about 0.3 wt. % of hydrogen peroxide and about 10 parts per million by weight of diethylene triamine pentaacetic acid or a salt thereof, all based on the total weight of (A) and (B).

Also contemplated are compositions as defined above which have been subjected to a heat treating step at a temperature of from about 50 to about 100 degrees C.

The invention further provides compositions as defined above which are substantially free of chloride, nitrate, nitrite, other metal salts, nitrosamine, formaldehyde, formaldehyde-yielding materials, cupric2 ions and non-aqueous solvents as well as compositions as defined above wherein there is present more than a trace amount of a compound selected from chloride, nitrate, nitrite, other metal salts, formaldehyde, a formaldehyde-yielding material, a non-aqueous solvent or a mixture of any of the foregoing.

In addition the invention provides compositions which also include an effective amount of a compound for improving the solubility of said 3-isothiazolone in water.

In a principal aspect the present invention provides methods for the production of a stabilized composition, said methods comprising:

(1) providing (A) an aqueous solution comprising at least one 3-isothiazolone compound of the general Formula I or II:

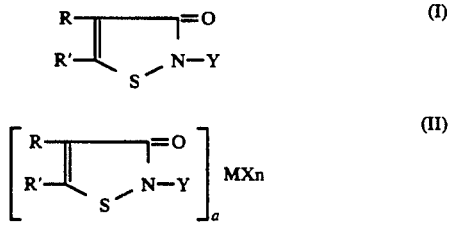

wherein

Y is a hydrogen atom or an unsubstituted alkyl group of from about 1 to about 18 carbon atoms, an unsubstituted or halo substituted alkenyl or alkynyl group of from about 2 to about 8 carbon atoms, an unsubstituted or substituted cycloalkyl group of from about 5 to about 8 carbon atoms, an unsubstituted or substituted aralkyl group of from about 7 to about 11 carbon atoms or an unsubstituted or substituted aryl group of from about 6 to about 10 carbon atoms;

R and R' are each selected from hydrogen, halogen or an alkyl group of from about 4 to about 8 carbon atoms;

M is a cation selected from a metal cation, an ammonium cation or an ammonium cation substituted with at least one organic group, a pyridinium cation or a pyrimidinium cation;

X is an anion forming a compound with the cation M; and a is 1 or 2 and n is a whole number which satisfies the valence of the cation M when completely reacted with anion X, alone, or in further combination with a stabilizer for I or II; and (2) intimately mixing therewith (B) a small effective amount of (i) a hydroperoxide-free organic oxidizing agent, alone, or in further combination with a stabilizer therefor;

(ii) a manganese-free inorganic oxidizing agent, alone, or in further combination with a stabilizer therefor; or (iii) a mixture of (i) and (ii).

Preferred features comprise such methods wherein component (A) comprises from about 0.5 to about 3 wt. % of said 3-isothiazolone and component (B) comprises at least about 0.1 wt. % based on the total weight of (A) and (B); a method as defined above wherein said inorganic oxidizing agent (i) comprises hydrogen peroxide, sodium perborate or a mixture thereof; a method as defined above wherein said organic oxidizing agent (ii) comprises benzoyl peroxide, tert.-butyl peroxide or a mixture thereof; a method as defined above which also includes using diethylene triamine pentacetic acid as a stabilizer for the oxidizing agent; a method as defined wherein said oxidizing agent (B) is present in an amount of from about 0.1 to about 3 wt. % based on the total weight of (A) and (8); and a method as defined which also includes using a stabilizer for the oxidizing agent and said stabilizer is present in an amount of from about 1 to about 20 parts per million by weight, based on the total weight of (A) and (B).

Special mention is made of methods as defined above wherein said 3-isothiazolone comprises: 5-chloro-2-methyl-3-isothiazolone; 2-methyl-3-isothiazolone; 2-octyl-3-isothiazolone; 4,5-dichloro-2-cyclohexyl-3-isothiazolone; 4,5-dichloro-2-octyl-3-isothiazolone; or a mixture of any of the foregoing.

Preferred is a method as defined above comprising (1) providing an aqueous solution comprising from about 1.0 to about 1.5 wt. % of a 5-chloro-3-isothiazolone, and (2) intimately mixing it with about 0.3 wt. % of hydrogen peroxide and about 10 parts per million by weight of diethylene triamine pentaacetic acid, all based on the total weight of (A) and (B); and a method as defined above which also includes: (3) subjecting the intimate admixture of (A) and (B) to a heat treating step at a temperature of from about 50 to about 100 degrees C. for a time at least lomg enough to provide enhanced stability; as well as a method wherein both (A) and (B) are substantially free of chloride, nitrate, nitrite, other metal salts, nitrosamine, formaldehyde, formaldehyde-yielding materials, cupric ions and non-aqueous solvents; and a method as defined above wherein in the intimately mixed composition there is also present more than a trace amount of a compound selected from chloride, nitrate, nitrite, other metal salts, formaldehyde, a formaldehyde-yielding material, a non-aqueous solvent or a mixture of any of the foregoing; and a method wherein the intimate mixture of (A) and (B) also includes an effective amount of a compound for improving the solubility of said 3-isothiazolone in water.

A further major aspect of the invention provides a method for preventing the growth of an organism selected from bacteria, fungi, yeasts, algae, or combinations of any of the foregoing, said method comprising bringing into the locus occupied by said organism or organisms an effective amount of a stabilized 3-isothiazolone solution as first defined above.

DETAILED DESCRIPTION OF THE INVENTION

The manufacture of 3-isothiazolones is described in U.S. Pat. No. 3,523,121; U.S. Pat. No. 3,517,022; U.S. Pat. No. 3,761,488 and U.S. Pat. No. 3,849,430. The solutions in accordance with the invention contain as 3-isothiazolone preferably 5-chloro-3-isothiazolone, particularly 5-chloro-2-methyl-3isothiazolone (CAS No. 26 172-55-4) as well as 2-methyl-3-isothiazolone, 2-octyl-3-isothiazolone, 4,5-dichloro-2-cyclohexyl-3-isothiazolone and/or 4,5-dichloro-2-octyl-3-isothiazolone.

The 5-chloro-2-methyl-3-isothazolone is preferably added in the solutions in accordance with the invention an a quantity of 1.0 to 1.5 wt. % taken on the whole solution.

In the manufacture of 5-chloro-2-methyl-3-isothiazolone there arise as by-products unchlorinated 2-methyl-3-isothiazolone of the following Formula III and in very small concentration 4,5-dichloro-2-methyl-3-isothiazolone of the following Formula IV or their complexes of the following general Formulae V and VI:

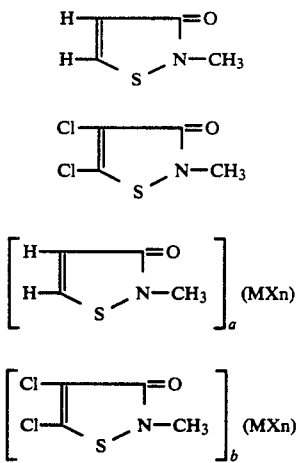

in which M, X, n, a and b have the preceding meanings.

In accordance with a particular embodiment of the invention the solution contains 1.0 to 1.5 wt. % of a 5-chloro-3-isothiazolone, 0.3 wt. % hydrogen peroxide and 10 ppm diethylene triamine pentaacetic acid, in each case taken on the whole solution.

For the use of the solution composed in accordance with the invention, it has been shown to be expedient to subject it to a heat treatment at a temperature of 50 to 100 degrees C. This has, for example, the advantage that the hydrogen peroxide concentration to be added for stabilization can be reduced.

The solution in accordance with the invention is particularly preferred if it is free of chloride, nitrate, nitrite, other metal salts, nitrosamine, formaldehyde, formaldehyde-yielding substances, $Cu^{2+}$ ions and/or solvents, with the exception of water.

For particular cases where applications require, however, it can be suitable or sufficient if the solution in accordance with the invention still contains chloride, nitrate, nitrite, another metal salt, formaldehyde, a formaldehyde-yielding material and/or a solvent. In such cases however these known stabilizers can be used in smaller concentrations than would be possible without the oxidizing agent added in accordance with the invention.

With some 3-isothiazolones it is advantageous if the solution in accordance with the invention additionally contains a material for improving the solubility of the 3-isothiazolone in water.

The manufacture of the solutions in accordance with the invention typically is accomplished in customary fashion by the dissolution of the corresponding 3-isothiazolone hydrochloride in water and subsequent neutralization with metal hydroxides or oxides.

Solutions in accordance with the invention which are free of inorganic neutralizing salts are obtained by the neutralization of the 3-isothiazolone hydrochloride with, for example, organic bases such as trimethylamine, triethylamine, tripropylamine, and cyclic tertiary amines, for example, pyridine, followed by extraction with an organic solvent.

The solutions in accordance with the invention can also contain one or more different biocides for improving their biocidal action. Among these are also biocides which yield a synergistic biocide combination with the 3-isothiazolones.

The solutions in accordance with the invention are preferably used for the prevention of growth of bacteria, fungi, yeasts or algae and can thus, for example, be used in the following areas: disinfecting agents (both in the medical area and for hospitals as well as laundries), sanitary cleaners, general cleaning agents, deodorants, liquid and powder soaps, oil and grease removers, dairy chemicals, wood preserving agents, dyes, varnishes, mordants, mold protecting agents, metal working liquids, coolong water, air cleaners, crude oil processing, paper treatment, paper mill slime prevention agents, adhesives, textiles (including non-wovens), pigment pastes, latexes, tanning agents, leather treatment agents, fuels, agents for use in agriculture and in mining, dyes, storage of crude oil, agents for swimming baths, rubber, cosmetics, toilet articles, pharmaceuticals, chemical cleaners, household washing agents, fuel additives, cutting oils, protective and decorative films, plastics, emulsions, waxes and polishes. Quite generally the solutions in accordance with the invention are suited for use in cases in which water and organic materials can in appropriate conditions come into contact with one another which would permit an undesired growth of microorganisms.

DESCRIPTION OF THE PREFERRED EMBODIMENTS

The following examples illustrate the compositions and methods of the present invention. They are not intended to limit the scope of the invention in any manner whatsoever.

EXAMPLES 1-7

The stability of aqueous solutions which contained a combination of 5-chloro-2-methyl-3-isothiazolone were tested in combination with various stabilizers. Additionally, the solutions were stored at elevated temperatures and then tested.

It is known that in accordance with the following program of elevated storage temperatures, one can determine the storage stability of such solutions at normal temperature. A storage time of one week at 50 degrees C corresponds to a storage time of 2 months at normal temperature, i.e., 25 degrees C. A storage time of 2 weeks at this higher temperature corresponds to a storage time of 4 months at normal temperature, a storage time of 3 weeks at this higher temperature corresponds to a storage time of 6 months at normal temperature, a storage time of 4 weeks at this higher temperature corresponds to a storage time of 8 months at normal temperature, and so forth.

Storage during a week at a temperature of 65 degrees C. corresponds to a storage of 7 months at normal temperature, a storage of 2 weeks at this higher temperature corresponds to a storage of 14 months at normal temperature, a storage if 3 weeks at this higher temperature corresponds to a storage of 21 months at normal temperature, etc.

An aqueous solution with a content of 1.5 wt. % of a mixture of 5-chloro-2-methyl-3-isothiazolone and 2-methyl-3-isothiazolone (wt. ratio 3:1) was made. For this the corresponding isothiazolone hydrochloride was neutralized in aqueous solution with dilute potassium hydroxide solution up to a pH value of 3.5. Then the respective stabilizers were added as is shown in the following Tables I, II, and III.

The solutions obtained were subjected to the above-noted storage test at temperatures of 50 and 65 degrees C. and then checked in accordance with the period of time given below by means of high pressure liquid chromatography (HPLC) for their residual isothiazolone content. With a residual quantity of at least 85 wt. % of the 3-isothiazolone, the solution was judged as sufficiently stable.

In the Tables I, II and III the symbols have the following meanings:

+ means greater than 85 % of the 3-isothiazolone remaining 0 means greater than 50 % and less than 85 % of the 3-isothiazolone remaining — means less than 50 % of the 3-isothiazolone remaining In Table I, the values of residual 3-isothiazolone are after storage at a temperature of 50 degrees C. The corresponding values in Tables II and III were obtained after storage at a temperature of 65 degrees C.

In the Tables the percentage data and the quantities in "ppm" refer in each case to the weight of the entire solution.

TABLE 1

| Stabilizer | Storage time, Weeks, 50 deg C. | | | | | | | | |
|---|---|---|---|---|---|---|---|---|---|
| | 1 | 2 | 3 | 4 | 5 | 6 | 8 | 10 | 12 |
| without (Control) | — | — | — | — | — | — | — | — | — |
| 0.3% hydrogen peroxide (Ex 1) | + | + | + | + | + | 0 | — | — | — |
| 0.3% hydrogen peroxide and 10 ppm DPTA (Ex 2) | + | + | + | + | + | + | + | + | + |
| 0.5% hydrogen peroxide and 1.5% magnesium nitrate (Ex 3) | + | + | + | + | + | + | + | + | — |
| 2% sodium perborate (Ex 4) | + | + | + | + | + | + | 0 | — | — |
| 2% sodium perborate and 0.1% DPTA (Ex 5) | + | + | + | + | + | + | 0 | 0 | — |

TABLE II

| C Stabilizer | Storage time, Days, 65 deg | | | | | |
|---|---|---|---|---|---|---|
| | 2 | 4 | 6 | 8 | 10 | 12 | 14 |
| without (Control) | — | — | — | — | — | — |
| 0.3% hydrogen peroxide (Ex 1) | + | + | 0 | — | — | — | — |
| 0.3% hydrogen peroxide and 10 ppm DTPA (Ex 2) | + | + | + | + | + | + | 0 |
| 2% sodium perborate (Ex 4) | + | + | + | + | 0 | — | — |
| 2% sodium perborate and 0.1% DTPA (Ex 5) | + | + | + | + | + | 0 | — |
| 0.3% hydrogen peroxide and 0.05% phosphoric acid (Ex 6) | + | + | + | 0 | — | — | — |
| 1.5% magnes. nit. (pr art) | — | — | — | — | — | — | — |

Corresponding to the above-noted tests, also tested were the stabilities of solutions which contained 1.5 wt. % of a chloride free mixture of 5-chloro-2-methyl-3-isothiazolone and 2-methyl-3-isothiazolone (weight ratio 3:1). These solutions were treated with the stabilizers given in Table III. The results are given in Table III.

TABLE III

| C Stabilizer | Storage time, Days, 65 deg | | | | | |
|---|---|---|---|---|---|---|
| | 1 | 3 | 5 | 10 | 12 | 15 |
| without (Control) | — | — | — | — | — | — |
| 0.3% hydrogen peroxide and 10 ppm DPTA (Ex 2) | + | + | + | + | + | 0 |
| 1.5% magnes. nit. (pr art) | — | — | — | — | — | — |
| 2.0% potas. nit. (pr art) | — | — | — | — | — | — |
| 1.2% magnes. sulf. (pr art) | — | — | — | — | — | — |
| 1.2% magnesium sulfate and 0.3% hydrogen peroxide and 10 ppm DTPA (Ex 7) | + | + | + | + | + | + |

From Tables I, II and III, it is evident that the stabilizers used in accordance with the invention, namely hydrogen peroxide and sodium perborate are superior to the known stabilizers magnesium nitrate, potassium nitrate and magnesium sulfate, particularly after storage at a temperature of 65° C.

EXAMPLE 8

A solution in accordance with the invention was compared with a 3-isothiazolone solution stabilized by nitrates in a known fashion with reference to the minimum inhibition concentration for bacteria according to the Boillon dilution method in accordance with DIN 58 940, Part 5. Aqueous solutions of a mixture of 5-chloro-2-methyl-3-isothiazolone and 2-methyl-3-isothiazolone (weight ratio 3:1) were used, The respective stabilizers, quantities of materials and bacteria are set forth on the following Table IV:

TABLE IV

| Test | Content of 3-isothiazolone in the solution % | Content of Stabilizer | Minimum inhibition concentration*, ppm 3-isothiazolone | | | |
|---|---|---|---|---|---|---|
| | | | Pr. vul. | Ps. ae. | Kl. ae. | Esch. c. |
| 1 (pr art) | 1.5 | 4% Mg (NO₃)₂ | 1 | 1 | 1 | 1 |
| 2 (pr art) | 1.5 | 1.5% Mg (NO₃)₂ and 0.15% Cu (NO₃)₂ | 0.5 | 0.5 | 0.5 | 0.5 |
| 3 (Ex 8) | 1.5 | 0.3% H₂O₂ and 10 ppm DPTA | 0.5 | 0.5 | 0.5 | 0.5 |

*Pr. vul = Proteus vulgaris 2.2 × 10⁶
Inoculum Concentration:
Ps. ae = Pseudomonas aeruginosa 2.4 × 10⁶
Kl. ae = Klebsiella aerogenes 8.0 × 10⁶
Esch. c. = Escherichia coli 2.2 × 10⁶

In Table IV it is evident that the minimum inhibition concentration of the solution in accordance with the invention (Example 8) corresponds to the minimum inhibition concentration of solutions stabilized in known fashion. This means that the oxidizing agent used as stabilizer in accordance with the invention does not adversely affect the minimum inhibition concentration but simultaneously creates the possibility of avoiding undesired nitrates as stabilizers.

EXAMPLE 9

A solution in accordance with the invention was compared with solutions stabilized in known fashion of 3-isothiazolones with respect to activity against fungi and yeasts with the agar diffusion tests according to DIN 58 940, Part 3. In the three subsequently given Formulations 1, 2 and 3, an aqueous solution of a mixture of 5-chloro-2-methyl-3-isothiazolone and 2-methyl-3-isothiazolone (weight ratio 3:1) was used in each case.

Formulation 1 (prior art):
Content of 3-isothiazolone: 1.5%
Stabilized with: 4% Mg (NO₃)₂
Neutralization salt: 0.9% MgCl₂

Formulation 2 (prior art):
Content of 3-isothiazolone: 1.5%2
Stabilized with: 1.5% mg (NO₃)₂ and 0.15% Cu (NO₃)₂
Neutralization salt: 0.9% MgCl₂

Formula 3 (Example 9):
Content of 3-isothiazolone: 1.5%
Stabilized with: 0.3% H₂O₂ and 10 ppm DTPA
Neutralization salt: 1.15% KCl The results are collected together in the following Tables V and VI:

TABLE V

| Formulation | 3-Isothiazolone concentration ppm | Inhibition zone on Malt agar, mm Species* | | | | |
|---|---|---|---|---|---|---|
| | | Asp. nig. | Fus. sp. | Pen. fun. | Sac. cer. | Rho. rub. |
| 1 (prior art) | 15 | 2 | 0 | 4 | 2 | 1 |
| | 22.5 | 3 | 1 | 5 | 3 | 2 |
| | 30 | 3 | 2 | 6 | 3 | 3 |
| 2 (prior art) | 15 | 1 | 0.5 | 5 | 1 | 2 |
| | 22.5 | 2 | 2 | 6 | 2 | 3 |
| | 30 | 3 | 3 | 7 | 3 | 4 |
| 3 (Example 9) | 15 | 2 | 1 | 5 | 2 | 2 |
| | 22.5 | 3 | 2 | 6 | 3 | 3 |
| | 30 | 3 | 3 | 7 | 4 | 4 |

*Asp. nig. = Aspergillus niger
Fus. sp. = Fusarium sp.
Pen. fun. = Penicillium funiculosum
Sac. cer. = Saccharomyces cerevisiae
Rho. rub. = Rhodotorula rubra

TABLE VI

| Formulation | 3-Isothiazolone concentration ppm | Inhibition zone on dextrose agar, mm Species* | | | | |
|---|---|---|---|---|---|---|
| | | Asp. nig. | Fus. sp. | Pen. fun. | Sac. cer. | Rho. rub. |
| 1 (prior art) | 15 | 1 | 0.5 | 4 | 2 | 1 |
| | 22.5 | 2 | 2 | 5 | 3 | 2 |
| | 30 | 3 | 3 | 6 | 3 | 3 |
| 2 (prior art) | 15 | 2 | 1 | 4 | 1 | 2 |
| | 22.5 | 3 | 2 | 5 | 2 | 3 |
| | 30 | 3 | 4 | 6 | 3 | 4 |
| 3 (Example 9) | 15 | 1 | 1 | 4 | 1 | 2 |
| | 22.5 | 2 | 2 | 5 | 2 | 3 |
| | 30 | 3 | 2 | 6 | 3 | 4 |

*See Table V

From Tables V and VI it is evident that the solutions in accordance with the invention have at least just as great an effectiveness as the solutions stabilized in known fashion.

EXAMPLE 10

The action of a solution in accordance with the invention on a 30 percent pure acrylate emulsion was tested. In comparison thereto in known fashion stabilized 3-isothiazolone solutions were tested. The Formulations 1, 2 and 3 given in the following Table VII had the same composition as that in Example 9.

On using polymer emulsions with preserving agents in the form of isothiazolones which contain neutralizing salts with divalent metal ions such as Mg²⁺ and Cu²⁺ a so-called salt shock can arise, i.e., there forms a bottom layer or a gelatine-like composition. This is naturally undesired.

For the above noted comparison first the polyacrylate emulsion was fed through a sieve (325 Mesh) in order to remove any gel which might have arisen from the manufacture of the emulsion.

Then in each case a sample of the emulsion was treated with the said Formulation 1, 2 or 3 wherein a concentration of 37.5 ppm of 3-isothiazolone, taken on the whole mixture, was added. The 3-isothiazolone solution was added to 100 g of the emulsion which was located in a 100 ml bottle with screw closure. The mix was mixed up well and stored at room temperature for one hour. Then the mix was fed through a sieve (325 Mesh) the residue retained by the sieve was washed with deionized water in order to remove non-coagulated emulsion from it. The residue on the sieve was collected together and dried overnight at a timperature of 50 degrees C. as well as then for an hour at 150 degrees C.

The results are given in the following Table VII:

TABLE VII

| Formulation | Sieve residue, mg/kg Emulsion |
|---|---|
| 1 (prior art) | 2072 |
| 2 (prior art) | 933 |
| 3 (Example 10) | no residue |

The results in the Table VII demonstrate that use of the stabilized solutions in accordance with the present invention provides no decomposition of the emulsions due to salt shock, a result with substantial and significant advantages in the manufacture of coating compositions, and the like.

The above-mentioned patents, publications and Test Methods are incorporated by reference.

Many variations of the present invention will suggest themselves to those skilled in this art in light of the above, detailed description. All such obvious variations are within the full intended scope of the appended claims.

I claim:

1. A stabilized composition comprising in intimate admixture:

(A) an aqueous solution comprising at least one 3-isothiazolone compound of the general Formula I or II:

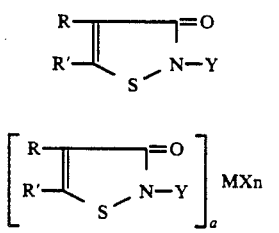

wherein

Y is a hydrogen atom or an alkyl group of from 1 to 18 carbon atoms, an alkenyl or alkynyl group of from 2 to 8 carbon atoms, a cycloalkyl group of from 5 to 8 carbon atoms, an aralkyl group of from 7 to 11 carbon atoms or an aryl group of from 6 to 10 carbon atoms;

R and R' are each selected from hydrogen, halogen or an alkyl group of from 4 to 8 carbon atoms;

M is a cation selected from a metal cation, an ammonium cation or an ammonium cation substituted with at least one organic group, a pyridinium cation or a pyrimidinium cation;

X is an anion forming a compound with the cation M; and a is 1 or 2 and n is a whole number which satisfies the valence of the cation M when completely reacted with anion X, alone, or in further combination with a stabilizer for I or II; and (B) a small effective stabilizing amount for said 3-isothiazolone compound of at least 0.1 wt. %, based on the whole solution, of a manganese-free inorganic oxidizing agent comprising hydrogen peroxide, sodium perborate or a mixture thereof, in combination with a stabilizer for said oxidizing agent, with the proviso that the ratio of weight percent of hydrogen peroxide to weight percent of isothiazolone is no more than about 0.33 and the ratio of weight percent of sodium perborate to weight percent of isothiazolone is no more than about 1.33.

2. A composition as defined in claim 1 which comprises diethylene triamine pentacetic acid as a stabilizer for the oxidizing agent.

3. A composition as defined in claim 1 wherein said oxidizing agent (B) is present in an amount of from 0.1 to 0.3 wt. % based on the whole solution.

4. A composition as defined in claim 1 wherein said stabilizer is present on an amount of from 1 to 20 parts per million by weight, based on the whole solution.

5. A composition as defined on claim 1 wherein said 3-isothiazolone comprises: 5-chloro-2-methyl-3-isothiazolone; 2-methyl-3-isothiazolone; 2-octyl-3-isothiazolone; 4,5-dichloro-2-cyclohexyl-3-isothiazolone; 4,5-dichloro-2-octyl-3-isothiazolone; or a mixture of any of the foregoing.

6. A composition as defined in claim 1 comprising from 1.0 to 1.5 wt. % of a 5-chloro-3-isothiazolone, from 0.1 to 0.3 wt. % of hydrogen peroxide and from 1 to 10 parts per million by weight of diethylene triamine pentaacetic acid or a salt thereof, all based on the whole solution.

7. A composition as defined in claim 1 which has been subjected to a heat treating step at a temperature of from 50 to 100 degrees C.

8. A composition as defined in claim 1 which is substantially free of nitrate, nitrite, other metal salts, nitrosamine, formaldehyde, formaldehyde-yielding materials, cupric ions and non-aqueous solvents.

9. A composition as defined on claim 1 wherein there is present more than a trace amount of a compound selected from chloride, nitrate, nitrite, other metal salts, formaldehyde, a formaldehyde-yielding material, a non-aqueous solvent or a mixture of any of the foregoing.

10. A composition as defined in claim 1 which also includes an effective amount of a compound for improving the solubility of said 3-isothiazolone in water.

11. A composition as defined in claim 4 wherein said stabilizer is present in an amount of from 1 to 10 parts per million by weight.

12. A composition as defined in claim 11 wherein said oxidizing agent comprises hydrogen peroxide and said stabilizer therefor comprises diethylene triamine pentacetic acid or a salt thereof.

* * * * *